United States Patent [19]

Hoots et al.

[11] Patent Number: 4,966,711
[45] Date of Patent: Oct. 30, 1990

[54] TRANSITION METALS AS TREATMENT CHEMICAL TRACERS

[75] Inventors: John E. Hoots, St. Charles; Rodney H. Banks, Naperville; Donald A. Johnson, Batavia, all of Ill.

[73] Assignee: Nalco Chemical Company, Naperville, Ill.

[21] Appl. No.: 315,713

[22] Filed: Feb. 27, 1989

[51] Int. Cl.$^5$ .............................................. C02F 1/00
[52] U.S. Cl. ................................. 210/697; 210/696; 210/699; 210/744; 210/745; 210/759; 436/56; 422/3; 422/62; 73/861.07
[58] Field of Search ............... 210/745, 744, 759, 696, 210/697, 699; 436/2, 56, 148; 73/861.07, 61.2; 422/3, 62

[56] References Cited

U.S. PATENT DOCUMENTS

| | | | |
|---|---|---|---|
| 4,209,398 | 6/1980 | Ii et al. | 252/180 |
| 4,264,329 | 4/1981 | Beckett | 436/56 |
| 4,664,884 | 5/1987 | Mullins et al. | 210/699 |
| 4,777,140 | 10/1988 | Rudnick | 208/50 |
| 4,783,314 | 11/1988 | Hoots et al. | 210/745 |

OTHER PUBLICATIONS

Multifunctional Liquid Cooking Water Treatment, Nalco 2808.
Multifunctional Liquid Cooling Water Treatment, Nalco 2575.
Mechanisms of Organic Inhibitors Used in Cooling Water Corrosion Control.
Anayltical Use of Luminescence Induced Ultrasonically in Solution.
Chem Abstract CA89(6):48676q.
Chem Abstract CA93(16):160598z.
Chem Abstract 86(22):160888z.
Chem Abstract CA103(6):44359y.
Chem Abstract CA78(10):66481z.
Chem Abstract CA98(16):13688v.
Chem Abstract CA98(14):118849k.
Chem Abstract CA96(2):11308q.
Chem Abstract CA79(6):34978w.
Chem Abstract CA102(10):89283q.

*Primary Examiner*—Richard V. Fisher
*Assistant Examiner*—Krisanne Shideler
*Attorney, Agent, or Firm*—Venable, Baetjer, Howard & Civiletti

[57] ABSTRACT

Methods for utilizing transition metals as tracers in aqueous liquid systems are provided by this invention. Transition metals with low background levels in system waters are identified as preferred when soluble in said aqueous liquid systems. The transition metals show low levels of deposition on equipment scale and provide reliable information as to the process history of the liquid systems.

28 Claims, 2 Drawing Sheets

TRANSITION METALS AS TREATMENT CHEMICAL TRACERS

FIELD OF THE INVENTION

The present invention pertains to the utilization of transition metals as tracers to quantify the change in the level of treatment chemicals under static and changing operating conditions of liquid systems and to control feed rates of treatment chemicals into liquid systems. Further, transition metal concentration can be used to quantify important characteristics of the system such as total volume and amount of a liquid entering and/or leaving the liquid system.

BACKGROUND OF THE INVENTION

In a system involving a body of liquid to which a treating agent is added, maintaining the proper feed level for the agent is essential for optimal performance. An improper feed rate of treating agent can lead to serious problems. For example, severe corrosion and deposit formation can rapidly occur on heat-exchanger surfaces in cooling water systems when incorrect levels of treating agent are used. One common method of estimating the concentration of a treating agent focuses on measuring the level of an active component in the treatment formulation (e.g., polymeric scale inhibitor, phosphate, or organophosphate). That technique is often unsatisfactory due to one or more of the following problems:

background interferences from the system liquid or materials contained in the liquid;
analytical methods require bulky and costly equipment;
time-consuming, labor-intensive analyses are not compatible with continuous monitoring; and
inaccurate readings result from degradation or deposition of active component within the system.

An alternative method of determining treatment feed rates is to add tracer compounds to the formulation or system. This method helps circumvent the degradation, deposition, and background interference problems that commonly occur when measuring the level of an active component in a treatment formulation. However, quantitation of low tracer levels commonly magnifies problems associated with expensive equipment and time-consuming test methods. Additional factors which must be considered are cost and environmental acceptability of the tracer. For example, radioactive tracers are detectable at very low levels, but are generally expensive and unacceptable due to environmental and health concerns.

Ultimately, compounds selected as tags or tracers serve as indices to other chemicals present in an aqueous system. These tags or tracers are selected to fulfill certain criteria. For example, certain tracers are detectable by electronic devices on a continuous or semi-continuous basis. In addition, certain tracers provide measurements of concentration that are accurate, repeatable and/or capable of being performed on many different waters (i.e., clean, turbid, hard, soft, etc.) and variations of these waters. To achieve these goals, the tracer selected is preferably not present in significant quantities within the waters tested. In addition, the tracers selected must be quantifiable by tests that are not interfered with or biased by other chemical compounds normally present in the water to be tested. The tracers selected are preferably inert and stable in the treatment water and do not reduce the activity of the treatment chemicals themselves.

The tracers must be soluble in the waters to be tested and must be compatible with the treatment chemicals with respect to formation, storage, freeze-thaw recovery, etc. Most importantly, the tracers must show a minimal incorporation into the equipment scale as compared to the treatment chemicals. Incorporation is the transfer of tracer from the treated aqueous system to the surfaces of the system equipment. Last, the tracers should not present any sort of environmental problems in the event of discharge. To avoid costly disposal methods, it is preferable for the tracer to be functional at levels sufficiently low so that discharge does not pose a health concern. The tracer is preferably non-toxic at high concentrations. The tracer must be sufficiently safe so that its use at the concentrations desired conforms to all governmental regulations.

Chromium VI (e.g. bichromate, $Cr_2O_7^{-2}$) has been used as a tracer in cooling waters in industrial cooling water systems. However, the Environmental Protection Agency and Occupational Safety Hazard Administration have restricted the use of Chromium VI in industry. Also chromium (VI) is a reactive, oxidizing agent and alternative tracer compounds are needed.

The present invention is based on the discovery of a new class of tracer compounds that meet the above specified criteria.

SUMMARY OF THE INVENTION

It has been discovered that transition metals, as a class, will satisfy the criteria for use as tracers if they are soluble in the liquid medium to be tested. The transition metals have been found to exhibit minimal incorporation into equipment scale and typically exhibit much lower incorporation than the treatment chemicals used in the liquid systems. Measuring the concentration of the transition metals provides more accurate information as to the volume of liquid and the amount of treatment agent added to the liquid system. As a consequence, this invention provides methods for using transition metals as tracers and compositions containing transition metal tracers therein.

The transition metals have been found to perform better as tracers than some non-transition metals because their rate of incorporation into deposits in the system is much lower. The most preferred embodiments of this invention employ transition metals which show lower incorporation into deposits in the system than Chromium VI, such as vanadium.

Natural sources of makeup waters have been found to have very low concentrations of transition metals as compared to non-transition metals. For example, aluminum and sodium are non-transition metals which have been found to be present at high background levels in many makeup waters. Preferred embodiments of this invention are directed to those transition metals identified as having low background levels in the makeup waters of most industrial cooling water system, permitting lower concentrations to be used.

The transition metals Chromium VI and lead are excluded from those used in the present invention because their use is limited by governmental agencies.

DETAILED DESCRIPTION OF THE INVENTION

It is an object of the present invention to avoid all of the aforementioned problems by incorporating a transition metal compound as a tracer into a treatment formulation for industrial process waters to provide quantitative measurement and control of treatment chemical feed rate and performance.

The phrase "transition metal compound" as used herein is intended to include transition metal ions, oxyanions, cations and associated complexes which are soluble in water. This phrase is also intended to include those compounds which form these ions, cations, oxyanions and complexes in water. The water soluble species are especially suitable for quantitative measure. This measurement allows for the calculated control of the feed rate of water and water treatment chemicals in fluid systems such as industrial process waters.

Most industrial operations utilize some aqueous systems which must be treated before being transferred to the environment; recycled to the system or process; or fed to the system or process. Preferably, aqueous systems are contemplated by this invention which include, but are not limited to, domestic wastewater, process wastewater, cooling water systems, boiler water or any other aqueous system that is treated physically or chemically before use in a process, during use in a process or before discharge to the environment where it is necessary to quantify the effects of the physical or the chemical treatment. This invention can also be utilized in a broad range of aqueous, mixed aqueous/non-aqueous, or non-aqueous liquid systems where the level of physical or chemical treatment affects performance of the system.

The most preferred aqueous system contemplated by this invention involves the treatment of cooling waters used in cooling systems. Cooling systems used in industrial processes typically include multiple water flow pathways through heat-exchangers, multiple sources of "makeup" and "blowdown" water, and control means for maintaining desired process conditions. Desired process conditions may include proper chemical treatment concentrations, temperature, water flow rate, water quality, and pH. A simplified version of an industrial cooling water system is a pilot cooling tower (PCT) shown in FIG. 1.

Figure 1:
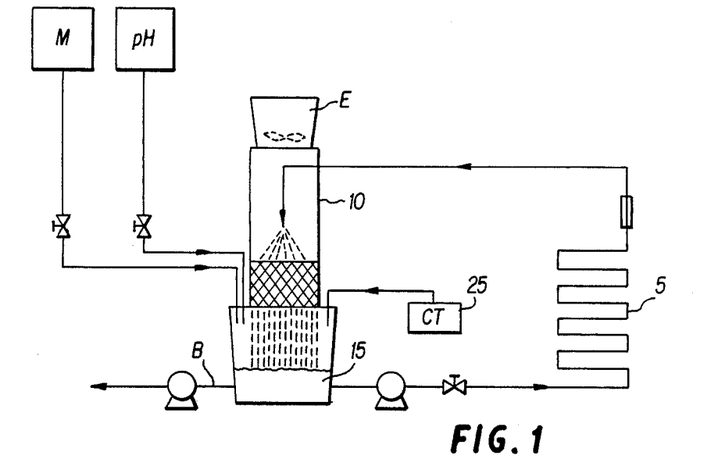
FIG. 1 — Is a schematic representation of a cooling water system, more specifically, a pilot cooling tower.

In pilot cooling towers, energy is extracted by the recirculating cooling water from the process-side of the system which is at a higher temperature by a heat exchanger (5). To maintain the efficiency of that heat transfer, energy is removed by evaporative cooling of the recirculating water in the cooling tower (10). Evaporation (E) of the cooling water leads to concentration of the suspended and dissolved solids in the cooled water (15). The concentration ratio (CR) is a measure of the increased level of dissolved and suspended matter in a system (eq 1), where CR ≧ 1.0.

$$CR = \frac{\text{concentration of salts in cooling water}}{\text{concentration of salts in makeup water}} \quad \text{(eq 1)}$$

The heat-exchanger surfaces need to remain clean to maintain efficiency. Deposition of solids and corrosion of heat-exchanger surfaces are problems most generally encountered. Cooling water systems commonly contain highly supersaturated levels of scaling salts. Deposition of solids throughout the system (particularly at metal heat-exchangers) will occur unless one or more chemical treatments (CT) such as scale inhibitors are added from source (25). To prevent corrosion of metal heat-exchangers and water transfer lines, chemical treatments commonly contain corrosion inhibitors. If the feed rate of the chemical treatment is too high or too low, severe scaling and corrosion can occur on the heat-exchangers and throughout the system.

It is vital that the level of dissolved and suspended solids, total volume of system's liquid and concentration of chemical treatment be maintained between certain values in order to provide economical usage of water, efficient heat transfer, minimal fouling of entire cooling system, and low operating costs. To maintain the concentration ratio (CR) within an acceptable range, water containing a "high" concentration of impurities must be removed from the system, collectively defined as "blowdown" (B), and replaced by water containing a "low" concentration of impurities, collectively defined as "makeup" (M). The value for concentration ratio, evaporation, blowdown and makeup water are variable due to changes in the weather, operating conditions of the industrial plant, and quality of the makeup water. Those factors are all interrelated and a change in any one of those factors must be counterbalanced by corresponding changes in other operating parameters.

In addition to the dynamic operating conditions of a cooling water system, other significant variables and unknown factors are commonly encountered. For example, blowdown water (B) can be removed from the cooling system through a variety of ways, some of which tend to be ill-defined in nature. The rate at which water is specifically pumped from the cooling water system is defined as "controlled water blowdown". Controlled water blowdown is not always accurately known due to practical difficulties in measuring large volumes of water. In addition, ill-defined amounts of recirculating water (un-accounted system losses) are commonly removed from the cooling water system to be used in other areas of the industrial plant, defined as "uncontrolled plant blowdown". Leakage of recirculating water and drift of liquid droplets from cooling tower also add to unaccounted system losses. A similar situation can occur with the makeup water, where the total makeup water rate (M) is the combined rate at which makeup water is specifically pumped into the recirculating system and liquid originating from other sources. The feed rate of chemical treatment into the cooling water system is commonly based on estimated values for recirculating water blowdown and makeup water pumped into the recirculating system which means there can be considerable uncertainty regarding the concentration of the chemical treatment. When operating conditions of the cooling water system change, the feed rate of the chemical treatment should be adjusted. Those adjustments may or may not be made, depending on how carefully the cooling water system is monitored and controlled. Even when feed rates are adjusted, the concentration of chemical treatment within a cooling water system generally may respond slowly to the change.

For example, where a system containing one million gallons has a total blowdown rate of 300 gal/min and the treatment feed rate is increased from 50 to 100 ppm, about 38.5 hours are required for only half of that change (25 ppm increase in treatment concentration) to be attained, assuming that no other fluctuations or changes have occurred within the system. For very large volumes and small values of blowdown, response time may be measured in days or weeks. In other cases, changes can occur rapidly, such as purposeful (or inadvertent) flushing of the system. Therefore, it is important that good control and accurate monitoring of the system be maintained.

Another significant operating parameter which should be quantified is holding time index (HTI), a measurement of the half-life of a chemical species within the system.

Under severe operating conditions, it is important to optimize HTI in order to reduce possible degradation of components in the chemical treatment without greatly increasing operating costs.

Due to all the operating limitations and uncertainties in cooling water systems, the need to rapidly determine and continuously monitor the concentration of chemical treatments is clearcut. The addition of a tracer to the chemical treatment permits accurate determination of all the known, imprecisely known, and variable operating conditions or "parameters" which vary with the composition of the liquid system, such as the present volume of a liquid system, the changes in volume of such a system, the quantity of treatment agent added to the system, the changes in the concentration of the treating agent and the lifetime of the treating agent within the system.

Transition metal compounds have been found which are soluble in aqueous systems as ions, oxyions, cations or associated complexes. Transition metal compounds have been found to be low in background presence within the makeup waters for substantially all industrial cooling towers, making their use as tracers very economical and efficient.

A survey of the system waters used in recirculating industrial cooling water systems suggests that the background presence of transition metal compounds within these waters is generally less than ppm. The background levels of most transition metal compounds within at least 80% of the system waters tested was found to be below 0.ppm. There have been some exceptions, such as zinc and iron; however, as a class, transition metals have been found to have a lower background presence in these waters than other metals such as aluminum, lithium, boron and strontium.

The preferred class of transition metal compounds include those which are soluble in aqueous liquid systems and show background levels of less than 0.01 ppm within 80% of the waters tested. These preferred transition metal compounds include those of cobalt, vanadium, titanium and yttrium.

Other members of the preferred class include those which show background levels of less than 0.1 ppm in 95% of the waters tested. These include those transition metal ions mentioned above, plus nickel, molybdenum (molybdate), and tungsten (tungstates). It is important that the tracer have low background presence within the makeup waters so as to limit the amount necessary to be added to function effectively as a tracer. It is preferable that the background level of a tracer provide no more than 10% of the signal which quantifies the level of transition metal in a sample.

Other transition metal compounds evaluated for use as tracers by this invention include those of copper, Chromium III and manganese. Ions of these transition metals are present as background in cooling water systems typically at relatively higher levels than the above mentioned transition metals, requiring higher levels to be added to the aqueous system and making them less cost effective.

Certain transition metals are well recognized as toxic at low levels and some have raised questions as to whether they pose health hazards to humans, i.e., carcinogens, mutagens, etc. For example, lead has long been recognized as toxic at very low levels and its use in gasoline has been restricted. Other species which raise health questions include cadmium and mercury. Each transition metal chosen (and the amount used) must conform to governmental guidelines. The use of Chromium VI has recently been regulated by the EPA and other governmental agencies. Consequently, lead, cadmium, mercury and Chromium VI are not considered suitable for use in this invention.

Other transition metal compounds are contemplated for use in the present invention; however, they are not preferred in that they are either present at high background levels in the makeup water for cooling water systems, or show poor solubility in aqueous liquid-systems. Examples of transition metal compounds which are excluded because they are insoluble in aqueous systems, or show very low solubility include those of zirconium and silver.

The transition metal compound chosen for any particular system must be soluble in the system, i.e. it must be ionized or dissociate to soluble ions, cations, etc. Additionally, the transition metal compound tracer should be chosen within those permitted by governmental guidelines. For example, OSHA and the EPA have restricted the use of Chromium VI in industry to the extent that its use as a tracer cannot be tolerated in all instances. In selecting a transition metal compound for use in a reducing environment, it may be desirable to choose metal ions which are in their lowest oxidation state or are weak oxidizing agents or are kinetically-stabilized towards reduction so that the metal tracer ions will not be reduced in their application. This conversion may interfere with the detection of such transition metals. For example, $Cr^{+6}$ can readily be reduced to $Cr^{+3}$, and may go undetected as $Cr^{+3}$ in subsequent quantification tests. On the other hand, Vanadium ($V^{+5}$), also referred to herein as Vanadium V, is a weak oxidizing agent in cooling water applications and tends to resist reduction to lower oxidation states which would not be detected by the analysis method. In addition, higher oxidation states beyond Vanadium V are not known so there is no concern with $V^{+5}$ tracers being converted to higher oxidation states which would not be detected by the analysis method. Since Vanadium V is already in its highest oxidation state there is no concern that it will be oxidized.

Soluble transition metals compounds are effectively used as cooling water treatment chemical tracers to allow the easy and accurate determination of chemical feed rates. These transition metal tracers may be added to the aqueous system directly but are preferably added to a treatment formulation such as a scale inhibitor or corrosion inhibitor. The addition of tracer compounds to liquid systems is very useful as a diagnostic tool for quantifying system characteristics and identifying and quantifying problems within the system. Also, the addition of a tracer to treatment formulations is very useful for measuring treatment concentration and efficacy.

Transition metal compounds offer a number of advantages as tracers. Nearly all transition metal compounds have negligible background levels in makeup waters so that interference is minimal. Many are not health hazards due to their low toxicity at the very low levels needed to function as tracers in most cooling systems. Additionally, most transition metal compounds when in the form of ions, cations, associated complexes, etc. are sufficiently inert, stable and soluble in a cooling water environment. The transition metal compounds are typically more stable than the treating agents which they "trace".

By means of a sensitive analytical method, preferably colorimetric, the transition metal compound concentration measured is used to determine the level of treating agents. Other possible methods of detecting transition metal concentration include ion selective electrodes, fluorometric analysis and voltametric analysis, as well as other conventional techniques for detecting ions.

As noted above, the preferred method of detecting transition metals is a colorimetric method. Colorimetry refers to the determination of a substance from its ability to absorb visible light. Visual colorimetric methods are based on a comparison of a blank or known solution with known concentration with that of a sample of unknown concentration. In spectrophotometric methods, the ratio of the intensities of the incident and the transmitted beams of light are measured at a specified wavelength by means of a detector such as a photocell or photomultiplier tube.

Molecular absorption in the ultraviolet and visible region depends on the electronic structure of the molecule. The energy absorbed elevates electrons from orbitals in a lower-energy state to orbitals in a higher-energy state. Since only certain states are possible in any molecule and the energy difference between any ground and excited state must be equal to the energy added, only certain frequencies can be absorbed. When a frequency that is absorbed by the molecule is found, the intensity of the incident energy is greater than the intensity of the emergent energy. Radiant power is defined as the radiant energy impinging on unit area in unit time. Transmittance is defined as the radiant power after the energy has passed through the absorbing solution and cell wall divided by the radiant power of the incident beam, [refer to Bauer, Christian and O'Reilly; "Instrument Analysis" (1978)].

Typically, in measuring the transmittance of a sample, a blank is made that contains all the reagents in solution except the compound of interest. Then, the measuring device is set at 100% for the blank. Thereafter, any reading of an actual sample will be the true absorbance minus any effects due to the holding cell or the reagent solution. The intensity of radiation absorbed in a thin layer of material depends on the absorbing substance and on the frequency of the incident radiation, and is proportional to the thickness of the layer. At a given concentration of the absorbing substance, summation over a series of thin layers, or integration over a finite thickness, lead to an exponential relationship between transmitted intensity and thickness. According to Beer's law, the amount of radiation absorbed or transmitted by a solution or medium is an exponential function of the concentration of absorbing substance present and of the length of the path of the radiation through the sample. Therefore, a plot of the absorbance, which is equal $-\log(\%T/100)$, versus concentration should give a straight line passing through the origin. When known concentrations of a compound are measured, a calibration curve, or in this case, a straight line, of the known concentration versus absorbance may be plotted. Finally, the samples with unknown concentration may be compared to the calibration curve to determine its concentration.

In the visible and ultraviolet regions, spectrophotometric methods may be used for the quantitative determination of many trace substances, especially inorganic elements. The basic principle of quantitative absorption spectroscopy lies in comparing the extent of absorption of a sample solution with that of a set of standards under radiation at a selected wavelength.

In many instances, the sample compound does not absorb radiation appreciably in the wavelength regions provided or the absorption is so low that it is desirable to form a light-absorbing tracer or at least better light-absorbing substance by reacting the compound in question with other reagents. The reagents should be selective in their reactions and should not form interfering absorbing species with foreign substances likely to be present.

Some of the factors that should be considered when forming light-absorbing compounds from tracer ions include: pH, reagent concentration, time, temperature, order of mixing reagents, stability, available masking agents, organic solvent, and salt concentration.

The pH plays a very important role in complex formation. Adjustment of pH or the use of a buffer often eliminates certain interfering reactions. Additionally, some transition metals are insoluble at high pH levels. One such metal is cobalt but it can be resolubilized by lowering the pH.

The amount of reagent required is dictated by the composition of the absorbing complex formed. An optimum concentration of reagents should be determined, since either not enough reagent or too much reagent can cause deviation from Beer's Law. Formation of the absorbing complex may be slow or fast with color development times ranging from several seconds to several hours. Therefore, in processes where time is of the essence, a complexing reagent that reacts quickly is important. Additionally, reaction rates are often affected by temperature. Certain reactions require elevated temperature to decrease the time necessary for complete color development.

Frequently, it is important to add the reagents in a specified sequence, otherwise full color development will not be possible or interfering reactions may occur. For instance, the highly selective color reaction of cobaltic nitrilotriacetate in the presence of hydrogen peroxide must be preceded by the formation of the cobaltous nitrilotriacetate complex. If the absorbing complex formed is not very stable, the absorbance measurement should be made as soon as possible. If the absorbing complex is photo-sensitive, precautions should be taken in order to avoid its photodecomposition.

The presence of masking agents are often necessary to prevent complexing of other reagents. For example, in the presence of excess EDTA, ferric ion does not form the colored $FeSCN^{2+}$ complex with a thiocyanate ion. Many organic reagents or complexes are only slightly soluble in water. In such cases, it is necessary to add immiscible organic solvent to avoid precipitation or to aid color development. Finally, it should be recognized that high concentrations of electrolyte often influence the absorption spectrum of a compound.

Transition metal compound concentrations when added to an aqueous system as tracers, can vary from parts per trillion (ppt) to parts per million (ppm). Detection of these compounds can be routinely accomplished on an instant or continuous basis with inexpensive portable equipment. In addition, multiple tracers may be used concurrently by choice of transition metal compounds with proper spectral characteristics or other tracers. As such, various combinations of transition metals and treatment feeds can be quantified within a liquid system. For example, several individual treatments containing different transition metal compounds can be employed within a liquid system. In that case, each transition metal compound and the corresponding individual concentration of each of the treatments can each be quantified. In addition to being able to quantify complex combinations of the treatment feeds, transition metal compounds are available which are environmentally acceptable, are not degraded by or deposited within the liquid systems, and are low in cost. The invention can generally be applied in the following ways:

(a) direct addition of from one or more transition metal compounds with or without other conventional tracers to a liquid system;

(b) incorporation of 1 to 6 (or even more) transition metal compounds into chemical treatment compositions containing other components wherein said treatment is applied to liquid system in order to maintain proper operation of that system;

(c) addition of 1 to 6 chemical treatment agents (or even more) containing transition metal compounds directly into liquid system or into liquid feed leading into system; and (d) addition of transition metal compounds without treatment agents so that within the liquid system individual tracer concentrations ranging from 1 part per trillion (ppt) to 100 parts per million (ppm), preferably from 1 part per billion (ppb) to 10 ppm, and most preferably from 10 ppb to 2 ppm are realized.

Figure 2:
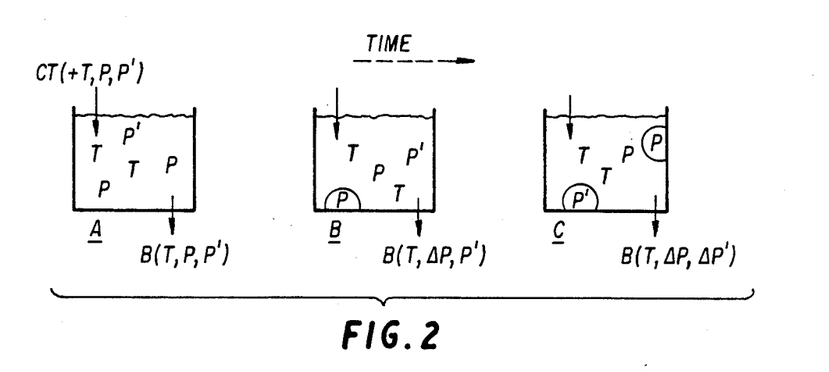
FIG. 2 — Is a representation of the effective concentration of recirculating water over time.

FIGS. 2A-C demonstrate the operation of the water treatment program at the molecular level as a function of time. In FIG. 2A, the concentration of chemical treatment (CT) contains phosphorus (P'), polymer (P) and tracer (T). This chemical treatment is slowly fed via feedline into the recirculating cooling water where the treatment is rapidly diluted and distributed throughout the system. If operating conditions of the cooling water system remained constant, the addition and removal of treatment due to recirculating water blowdown (B) would equilibrate. The concentration of the chemical treatment and its components ideally should remain unchanged. However, that situation never occurs. As time progresses (FIGS. 2B-C), additional amounts of polymer, and phosphorus-containing compounds can be lost from the recirculating water due to deposition and protective-film formation on metal surfaces and chemical/biological degradation processes. Also, changes in operating conditions (blowdown rate, concentration ratio, and product feed rate, and others) affects the concentration of the treatment components. Without a tracer, analysis of the recirculating water may measure current concentrations of some of the treatment components (assuming an analysis method exists), but cannot directly indicate the original feed rate of the treatment program. Use of a tracer to quantify and control the treatment feed rate is a valuable addition to current water treatment programs.

FIGS. 2A-C also indicate how addition of an inert tracer can provide accurate determination of treatment feed rate and treatment efficacy, in spite of deposition of other components in the chemical treatment. For example, assume the formulation feed rate was 100 ppm. If deposition occurred on the heat-exchangers, 40% of the phosphorus-containing species could be lost from the recirculating water, but little or none of the transition metal tracer will be lost. The total phosphorus concentration would suggest only 60 ppm of the product was present. However, the transition metal ion tracer would more closely indicate the formulation feed rate of 100 ppm and a loss of phosphorus-containing components equivalent to that supplied by 40 ppm feed of formulation was being deposited. Determination of loss rates of active component(s) of the treatment is a direct measurement of treatment efficacy.

One method of evaluating transition metal compounds as tracer compositions is to compare their measured deposit enrichment ratio (DER) (eq 2) against the DER values for the active components.

$$DER = \frac{\text{wt. \% species in scale deposit}}{\text{(ppm concentration species in circulating liquid)} \times 10^6} \quad (eq\ 2)$$

Figure 4:
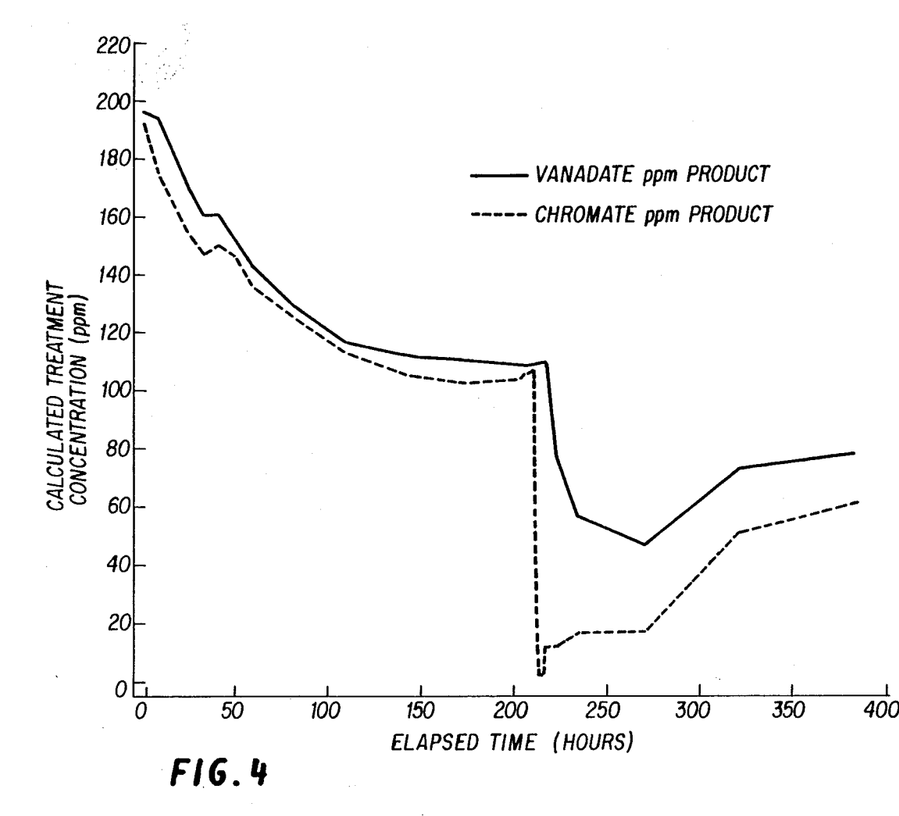
FIG. 4 — Is a graph of the chemical treatment concentration determinations on vanadate tracer and bichromate ($Cr_2O_7^{-2}$, where chromium is formally +6 oxidation state) tracer in a pilot cooling tower.

Preferably, the DER value of the tracer is lower than that of active and readily analyzed components of the treatment formulation. The lower the DER values under scale forming conditions the better. While low DER values are desired, the tracer compound should also exhibit good stability and not decompose when in use. For example, it is known that vanadium responds to pH changes more favorably than Chromium VI as shown in FIG. 4.

Important system characteristics of many industrial systems (total volume, blowdown, and makeup rates, holding time index, treatment feed rates and others) are imprecisely known, variable and sometimes unpredictable in nature. Lack of knowledge regarding those factors can lead to serious deposit and corrosion problems throughout the entire cooling water system. In particular, over/underfeeding of treatment program or improper operation of cooling water system can result in significant loss of treatment component(s) and adversely affect heat transfer within a cooling water system. In addition, water treatment programs commonly contain regulated or toxic materials (e.g. phosphate or chromate). Overfeeding of treatments can be hazardous and makes it more difficult for industrial sites to meet governmental restrictions on effluent discharges. Use of the transition metal tracers identified herein is a highly desirable means of accurately determining, continuously monitoring, and controlling cooling water system characteristics and treatment feed rates within desirable ranges.

Preferably, transition metals are used as chemical feed tracers in industrial cooling water systems. However, there are numerous examples of industrial systems whereby a chemical treatment is added to a moving liquid in a containment structure(s) and associated transfer lines in order to maintain proper operation of the system. In many cases, the concentration, feed rate and efficacy of the chemical treatment are imprecisely known and system characteristics (total volume, makeup and blowdown rates, holding time index, etc.) are estimated, variable or unknown. The systems can generally be divided into three major classes: closed, open, and once-through. In each case, transition metal can be effectively used to determine and continuously monitor the concentration and efficacy of chemical treatment and a system's operating conditions and unknown characteristics.

In a "closed" system, the liquid and chemical treatment generally remain within the system and minimal amounts of liquid are added or discharged. Common examples of closed systems are continuous casting processes in the metallurgical industry, refrigerating and air-conditioning units, radiator units, and recirculating cooling water systems in areas where water use or chemical discharges are severely limited. In those systems, the treatment can be lost through chemical/microbial degradation, deposition/corrosion processes, system leaks and low level discharges.

The common characteristics of "open" systems are that variable and significant amounts of liquid (makeup) and chemical treatment are added and discharged (blowdown) from the working fluid. The system may or may not be pressurized and subject to evaporative losses of fluid. Common examples of open systems are boilers, gas scrubbers and air washers, municipal sewage treatment, metal working and fabrication processes, paint spray booths, wood pulping and papermaking, and others. Chemical treatment can be lost through system discharges and leaks, deposition/corrosion processes, adsorption onto particulate matter, chemical/microbial degradation, etc.

"Once-through" systems generally involve a fluid and chemical treatment which are added to a system, pass through the system a single time, and then are discharged as effluent or transferred into another system. Much larger amounts of water are required in those systems than in comparable "closed" or "open" recirculating systems. Common examples of once-through systems are clarification and filtration units, mineral washing and benefaction, boilers, and cooling for utilities and industrial process streams.

In each of the above situations, the chemical treatment containing a known quantity of transition metal is added to and distributed within the liquid system. The liquid can be sampled or continuously monitored at any point of addition, from within the system or its discharge. By comparing absorbance of the system liquid with a standard solution containing a known concentration of chemical treatment and transition metal, the concentration of the chemical treatment within the liquid system may be determined. In addition, by determining the transition metal concentration at different points in the system, the uniformity of chemical treatment distribution and presence of low fluid flow and stagnant regions within the system can be quantified.

Figure 3:
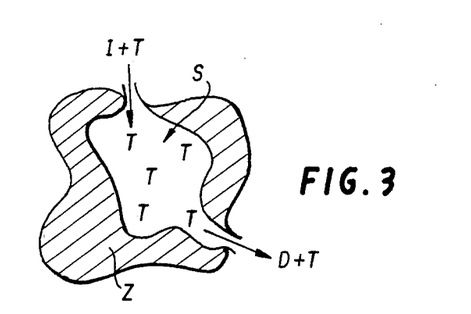
FIG. 3 — Is a representation of the effect of adding tracers to large volumes of liquid wherein the effective volume is much smaller than the true volume.

Stagnant or low fluid flow regions are inherent in some systems, in spite of continued addition and discharge of liquid(s). For example, oil field applications (drilling, secondary and tertiary recovery methods, etc.) involve addition of chemical treatment(s) to a liquid which will permeate slowly into some portions of a larger system. FIG. 3 shows that although the true total volume (Z) of that system cannot be accurately determined, the effective working volume (S) and average concentration of the chemical treatment can be quantified by comparing the tracer concentration in the liquid entering (I+T) and leaving the system (D+T). By comparing the individual concentrations of treatment components and transition metal tracer, the efficiency and degradation of the treatment and its components can be determined.

Based on the techniques described above, one may accurately determine many operating parameters (total volume, holding time index, blowdown rate, unaccounted for system losses, chemical treatment efficacy, etc.) within the wide variety of systems.

The successful use of transition metal ion tracers described above have been accomplished in several systems. The following examples are illustrative of particular embodiments of the invention. It is emphasized that not all embodiments of this invention are illustrated with the particularity given below. A typical calibration procedure is given below. To calibrate a spectrophotomer for measurement of Co II concentration, a series of solutions with known quantities of Co II were prepared.

SPECTROMETER CALIBRATION PROCEDURE FOR CO II

The samples of cobalt solutions in Table 1 were obtained from a 100 ppm stock solution of $Co(NO_3)6H_2O$ and diluted with water to the concentrations shown in Table 1. Fifteen ml samples of the stock solution were mixed with a mask mix and a color reagent. The mask mix consisted of an aqueous sodium citrate and sodium sulfite solution. The color reagent (PAR) solution consisted of 1–3 drops 0.1 N sodium hydroxide in approximately 50 mls of 0.2% pure pyridyl azo resorcinol in water. To the first sample only, 10 drops of ethylene diamine tetra acetic acid (EDTA) solution was added to simulate 100% dilution at 530 nm. The EDTA solution consisted of 5 gm $Na_2EDTA$ in 100 mls water with a pH adjustment to 9 with NaOH.

TABLE 1

| | Calibration Data for Cobalt II | |
|---|---|---|
| $[Co^{+2}]$ ppm | Percent Transmittance | Absorbance (A)* |
| 0** | 100 | 0 |
| .01 | 98 | .008 |
| .05 | 90 | .045 |
| .1 | 81 | .092 |
| .2 | 67 | .174 |
| .3 | 57 | .244 |
| .4 | 49 | .310 |
| .5 | 45 | .347 |
| .6 | 41 | .387 |
| .7 | 38 | .420 |
| 1.5 | 31 | .509 |

*(A) = $-\log(\%T/100)$.
**EDTA solution added to simulate 100% dilution.

Transmittance was measured with a Bausch and Lomb Spectrometer 2000 at a wavelength of 530 nm. The data from Table 1 was used to generate a calibration curve. The tracer concentration of samples with unknown tracer concentration was determined by comparison with the curve generated from the data above.

EXAMPLE 1

Use of Cobalt Compound ($Co^{+2}$) as Product Feed Tracer in Recirculating Water System Tests were conducted in an integrated scaling unit (ISU) designed to simulate an industrial cooling water system, such as the pilot cooling tower shown schematically in FIG. 1. The ISU contains a seven liter system adapted to receive continuous streams of water, chemical treatment and various tracers. This minimizes variations in concentrations of components during a test run. The streams are fed through syringe pumps that pump concentrated feed from a stock solution prepared in sufficient quantity to last an entire test period. The ISU is a recirculating water system which contains a metal heat-exchange tube and is used to model cooling water systems.

Continuous blowdown is accounted for by continuous makeup and chemical treatment addition. These tests were conducted to provide data that allows comparison of a cobalt tracer under various simulated treatment conditions against tracers with known performance. Here mainly, a cobalt tracer is evaluated by comparison of its performance with other available methods of detecting chemical treatment.

The % of expected feed is obtained by dividing the observed amount of tracer by the expected amount of tracer in the system multiplied by 100%. The expected amount of tracer is calculated by a mass balance of concentrated chemical feed added, makeup water added and blowdown water lost.

Comparison of Cobalt Tracer ($Co^{+2}$) with Aryl Sulfonic Acid Fluorescent Tracer and Active Phosohate Analysis This example serves to compare $Co^{+2}$ as a tracer against fluorescent tracers and direct measurement of the active phosphate treating agent.

The ISU was started wherein two syringe pumps were activated. The first pump injected a mixture comprising 57.3 weight percent deionized water, 1.1 weight percent aryl sulfonic acid fluorescent tracer, 36.6 weight percent acrylic acid base terpolymer and 1.0 weight percent $Co^{+2}$ as $Co(NO_3)_2 \cdot 6H_2O$ (5 weight percent). The second pump injected an overlay of a mixture including deionized water, potassium hydroxide, phosphate compounds, tetrapotassium pyrophosphate and phosphoric acid. The mixture injected from the first pump was diluted in the system water to 126.8 ppm. The mixture injected from the second pump was diluted in the system water to 170.3 ppm. Grab samples were analyzed for total phosphorous, fluorescent tracer and $Co^{+2}$. Table 2 shows the results. Transmittance was determined spectrophotometrically with a Bausch and Lomb Spectrometer 2000. The sample blank contained deionized water, EDTA, a mask mix and indicator. Samples include mask mix and indicator. The mask mix was a sodium citrate and sodium sulfite aqueous solution. The color reagent was a PAR solution as described above.

TABLE 2

Calculated Concentration of Chemical Feed Based on Tracers

| Time Elapsed (Hr) | ppm $Co^{+2}$ | % of Expected Chemical Feed* | | |
|---|---|---|---|---|
| | | Based on $Co^{+2}$ | Based on Fluorescent Tracer | Based on Active Phosphate |
| 0 | .32 | 87.4% | 96.8% | 102.9% |
| 19** | .094 | 24.4 | 53.5 | 20.0 |
| 45** | .091 | 24.4 | 39.4 | 11.8 |
| 50.75** | .098 | 27.6 | 34.6 | 20.0 |
| 63.75** | .121 | 36.2 | 28.7 | 13.5 |
| 66.25 | .254 | 76.4 | 94.5 | 81.8 |
| 87.75 | .206 | 63.8 | 104.7 | 63.5 |
| 95.25*** | .175 | 55.9 | 111.8 | 58.8 |
| 113.75*** | .119 | 36.2 | 116.5 | 38.8 |

TABLE 2-continued

Calculated Concentration of Chemical Feed Based on Tracers

| Time Elapsed (Hr) | ppm $Co^{+2}$ | % of Expected Chemical Feed* | | |
|---|---|---|---|---|
| | | Based on $Co^{+2}$ | Based on Fluorescent Tracer | Based on Active Phosphate |
| 117 | .337 | 103.9 | 110.2 | 102.4 |
| 120 | .278 | 85.0 | 112.6 | 83.5 |
| 136.5 | .349 | 107.0 | 114.2 | 92.4 |
| 144 | .355 | 109.4 | 115.0 | 89.4 |
| 159.75 | .318 | 97.6 | 115.0 | 95.9 |
| 164.25 | .339 | 103.9 | 128.3 | 95.3 |
| 166.5 | .324 | 97.6 | 118.1 | 95.9 |
| 188.75 | .402 | 122.0 | 126.8 | 95.9 |
| 210.25 | .403 | 122.0 | 126.8 | 92.8 |
| 231.75 | .384 | 115.7 | 126.8 | 96.5 |
| 239.5 | .404 | 122.0 | 126.8 | 107.1 |
| 261.25 | .426 | 131.5 | 133.1 | 104.7 |
| 279.75 | .410 | 125.2 | 125.0 | 100.0 |
| 303.75 | .429 | 131.5 | 128.3 | 102.4 |
| 311.25 | .430 | 131.5 | 128.3 | 97.6 |
| 334.75 | .474 | 143.3 | 126.8 | 104.7 |

*Values >110% of expected chemical feed will result from increase in concentration cycles of recirculating water due to slow evaporation of water from system.
**Test of tracer response based on loss of product feed.
***Out-of-specification operation to test effects of high pH excursion.

The purpose of the following analysis is to measure the difference between $Co^{+2}$ readings and fluorescent tracer readings and other active component(s) of the treatment.

Chemical Feed Determination Analysis

When 63.75 hours elapsed, the syringe pumps were started. After that point in time, there was an immediate rise in measured $Co^{+2}$ ion concentration as well as fluorescent tracer concentration and active phosphate. Next, the effect of a high pH upset was evaluated as the pH of the system was increased to 8.3. The measured $Co^{+2}$ ion concentration dropped to 0.119 ppm $Co^{+2}$ corresponding to 36.2% of the expected feed. At the same point in time, the fluorescent tracer concentration remained relatively high corresponding to 116.5 ppm concentration of treatment. When the pH was lowered to a normal operating value (pH 7.2) at an elapsed time of 117 hours, the measured $Co^{+2}$ ion concentration increased to a corresponding 103.9% of the expected chemical feed. The drop in pH below 8 increased dramatically the solubility of the $Co^{+2}$ ion in the system. Very good results were obtained with $Co^{+2}$, once the pH was controlled at a level below 8.0 during an elapsed time of approximately 136.5 hours to an elapsed time of approximately 279 hours. Also during that time, a 12,400 Btu/ft²/hr heater was turned on to increase the basin temperature to 100° F. and provide a heat transfer surface whereby deposit growth could occur. At an elapsed time of approximately 279 hours until the end of the test, a 25,000 Btu/ft²/hr heater was turned on to increase the basin temperature to 120° F. and very good results were still obtained with the $Co^{+2}$ tracer. The concentration of chemical treatment slowly increases with time due to constant evaporation of the process water throughout the test.

The concentration of $Co^{+2}$ ion was determined by the colorimetric technique described above. The fluorescent tracer concentration was determined by comparison of the samples with a calibration curve of tracer concentration versus emission, [refer to J. R. Lakowicz; "Principles of Fluorescence Spectroscopy" (1983)].

The total phosphorus content was determined by persulfate oxidation of organophosphorus species to orthophosphate and subsequent formation of blue phosphomolybdate complex which was quantified spectrophotometrically, [refer to M. C. Rand; "Standard Methods for the Examination of Water and Wastewater", 14th Ed. (1975)]. All concentrations of tracers and phosphorus containing species are expressed as % of expected chemical feed concentration.

This analysis shows that a Cobalt compound can function as a tracer and accurately determine the chemical treatment feed rate at pH $\leq 8$. The analysis proves that Cobalt compounds can follow the proven fluorescent tracers and are superior in determining treatment feed rates than by direct measurement of the treatment agent (e.g. total phosphorus concentration). This analysis shows that the $Co^{+2}$ may be accurately quantified in the presence of active chemical treatment agents, other tracers and other compounds and complexes commonly found in industrial water.

Deposit Analysis

The site of heaviest scaling was removed from a stainless steel heat exchanger within the ISU. The white deposit was readily dissolved in HCl. Table 3 shows the deposit enrichment ratio (DER) of the various components within the scale.

TABLE 3

| DER of Scale Formation Within ISU for Various Compounds | |
|---|---|
| Component | DER |
| Fluorescent Tracer | .01 |
| $Co^{+2}$ Ion | .92 |
| Ortho Phosphate | 1.04 |
| Total Phosphorus | 1.85 |
| Pyro Phosphate | 2.54 |
| Hydroxyethanediphosphonicacid (HEDP) | 4.25 |

The enrichment ratio data shows that the $Co^{+2}$ ion has less of a tendency to deposit in the above described system than active treatment formulation components and by-products such as ortho phosphate, pyro phosphate, total phosphorus and HEDP. Therefore, chemical feed determination using a $Co^{+2}$ ion is acceptable within the presence of the above-identified active treatment formulation. Note, also, that the $Co^{+2}$ ion enrichment ratio is deceptively high in this analysis because the system pH was brought above pH 8 allowing some precipitation of $Co^{+2}$ ion to occur.

EXAMPLE 2

A test was conducted in an integrated scaling unit (ISU) designed to simulate an industrial cooling water system with chemical treatment in the feed as described in Example 1.

Comparison of Cobalt Ion Tracer ($Co^{+2}$) with Aryl Sulfonic Acid Fluorescent Tracer, Lithium Ion Tracer and Active Phosphate Analysis The ISU was started wherein two syringe pumps were activated. The first pump injected an aqueous solution comprising 71.50 weight percent deionized water, 0.37 weight percent aqueous sodium hydroxide (50 weight percent aqueous), 14.44 weight percent aqueous potassium hydroxide (45 weight percent aqueous), 5.41 weight percent aqueous tetra potassium pyrophosphate (40 weight percent aqueous), 4.86 weight percent phosphoric acid (25 weight percent aqueous), 2.12 weight percent aqueous sodium tolyl triazole (50 weight percent aqueous), 1.21 weight percent aqueous HEDP (40 weight percent aqueous) and 0.10 weight percent aryl sulfonic acid fluorescent tracer. The second pump injected a mixture comprising 94.35 weight percent deionized water; 4.57 weight percent of a terpolymer consisting of an acrylic acid base, acrylamide and acrylamidomethane-sulfonic acid; 0.63 weight percent $Co(NO_3)_2 \cdot 6H_2O$ (1.0 weight percent $Co^{+2}$) and 0.45 weight percent LiCl (0.6 weight percent $Li^+$). The mixture injected from the first pump was diluted in the system with water to 132.3 ppm. The mixture injected from the second pump was diluted in the same system with the same water to 171.3 ppm. Grab samples were analyzed for total phosphorus, fluorescent tracer, lithium tracer and $Co^{+2}$ tracer. Table 4 shows the results. Transmittance was determined with a Bausch and Lomb Spectrometer 2000.

TABLE 4

| | Calculated Concentration of Chemical Feed Based on Tracers | | | |
|---|---|---|---|---|
| | % of Expected Chemical Feed | | | |
| Time Elapsed (Hr) | Based on $Co^{+2}$ Ion | Based on Fluorescent Tracer | Based on Lithium Ion | Based on Active Phosphate |
| 0 | 47 | 70 | 72 | 59 |
| 17.58 | 71 | 75 | 85 | 50 |
| 41.58 | 75 | 92 | 100 | 64 |
| 71.58 | 104 | 97 | 115 | 76 |
| 104.33 | 113 | 105 | 118 | 83 |
| 129.08 | 115 | 106 | 125 | 86 |
| 137.58 | 102 | 106 | 125 | 79 |
| 185.58* | 22 | 127 | 125 | 37 |
| 262.16* | 36 | 117 | 120 | 28 |

*Out-of-specification operation to test effects of high pH excursion.

The purpose of the following analysis is to compare $Co^{+2}$ tracer readings and fluorescent tracer readings and lithium ion tracer readings and other active components of the treatment.

Chemical Feed Determination Analysis

For the first approximately 185 hours during pump operation the pH was maintained at $7.0 \pm 0.3$. Scaling and corrosion were observed on the heat exchanger tube. Lithium ion tracer, fluorescent tracer and $Co^{+2}$ tracked closely while the active phosphate lagged behind. Under these conditions, the tracers were not significantly being incorporated into the scale deposits. Total Fe in the cooling water ranged from 0.5–0.6 ppm. At an elapsed time of 185.58 hours, the pH had increased to 8.0 Where it was noted previously that $Co^{+2}$ undergoes precipitation. As expected, $Co^{+2}$ levels dropped off. Only lithium and aryl sulfonic acid tracked near 100% expected feed.

The concentration of each component was determined as described in Example 1. The concentration of lithium ion was determined by conventional atomic absorption spectroscopy. All concentrations of tracers and phosphorus containing species are expressed as % of expected chemical feed.

This analysis shows that a $Co^{+2}$ ion can be used to accurately determine the chemical treatment feed rate. The analysis proves that $Co^{+2}$ ions follow the proven fluorescent tracers and perform very effectively as compared to other currently used methods for determining treatment feed rates. This analysis shows that the $Co^{+2}$ ions may be accurately quantified in the presence of active chemical treatment agents, other tracers and other compounds and complexes commonly found in industrial water.

EXAMPLES 1-2 — Conclusion

Since $Co^{+2}$ ion increases in solubility below pH=8, it may be desirable to use Cobalt tracers in water treatment systems with pH levels below 8. Ions, elements, and compounds commonly encountered in industrial cooling water systems (i.e. $Ca^{+2}$, $Mg^{+2}$, $HCO_3^-$/$CO_3^{2-}$, $PO_4^{-3}$, $P_2O_7^{-2}$, polymer and hydroxy ethane diphosphonic acid) do not affect performance of $Co^{+2}$ ions as total product feed tracer. Nevertheless, ions that respond to the color reagent (i.e. copper ions and iron ions) must be masked to prevent erroneous readings.

EXAMPLE 3

Use of $VO_3^-$ as Product Feed Tracer in Pilot Cooling Tower (PCT)

A test was conducted on a pilot cooling tower (PCT) designed to simulate an industrial cooling water system. The PCT contains a 50 liter capacity adapted to simulate recirculating water, chemical treatment feed, deposit formation and corrosion on heat exchangers, blowdown and makeup, and evaporative cooling from a tower fill. The test was conducted to provide data that allows comparison of a vanadate ion ($VO_3^-$) as a tracer under various simulated treatment conditions against a conventional chemical feed determination method.

Alternative Sample Analysis

As described in the calibration procedure, pyridylazo resorcinol (PAR) color reagent may be used successfully as an indicator with cobalt II ions when background ions are masked with a sodium citrate and sodium sulfite solution. When sampling $VO_3^-$, the sample is buffered at pH 5.5. The buffer converts $VO_3^-$ to $VO_2^+$, which reacts completely with the PAR solution. However, $VO_2^+$ also reacts with conventional masking agents. Therefore, $VO_2^+$ is hidden from detection when masking agents are present.

To eliminate the need for masking agents, $H_2O_2$ may be added to a sample solution before the PAR color reagent to form 2:1 diperoxyvanadate, $VO(O_2)_2^-$, which does not react with the PAR solution. To another sample, the $VO_2^+$ ions are allowed to completely react with the PAR solution. The difference in the transmittance between the two samples provides an indication of the concentration of vanadium ions present within the sample.

Comparison of Vanadate Ion Tracers ($VO_3^-$) with Active Phosohate Analysis A single water treatment formulation containing 54.55 weight percent deionized water, 16.1 weight percent aqueous sodium hydroxide (50 weight percent aqueous), 7.0 weight percent amino-tris (methylene phosphoric acid) (Dequest 2000 manufactured by Monsanto), 12.0 weight percent organo phosphonocarboxylic acid (50 weight percent aqueous), 4.7 weight percent sodium tolyltriazole (50 weight percent aqueous), 2.5 weight percent fatty dicarboxylic acid (Diacid 1550 distributed by WestVaco), 2.0 weight percent surfactant and 1.15 weight percent ammonium metavanadate with the $VO_3^-$ tracer level controlled at 0.5 ppm V at a 100 ppm product level. PCT test results are summarized in Table 5.

TABLE 5

Chemical Feed Determination Based on $VO_3^-$ Concentration, Active Phosphate Concentration and Blowdown Measurement

| | Calculated Concentration of Chemical Feed (ppm) | | |
|---|---|---|---|
| Time Elapsed | Based on $VO_3^-$ | Based on Active Phosphate | Based on Blowdown/ Syringe Measurement* |
| 200 ppm of product | 197 | 200 | — |
| 0 (startup) | 190 | 201 | — |
| 2.75 | 195 | 204 | — |
| 15.67 | 187 | 187 | — |
| 32.60 | 172 | 138 | — |
| 43.50 | 164 | 109 | — |
| 63.67 | 132 | 77 | — |
| 68.00 | 132 | 81 | — |
| 71.00 | 131 | 84 | — |
| 97.50 | 125 | 86 | — |
| 104.30 | 123 | 82 | — |
| 126.50** | 118 | 88 | — |
| 153.33 | 113 | 85 | 113 |
| 178.20 | 111 | 86 | 114 |
| 204.50 | 108 | 80 | 114 |
| 227.67 | 104 | 76 | 106 |
| 254.40 | 106 | 81 | 111 |
| 298.25 | 107 | 83 | 111 |
| 324.67 | 108 | 85 | 115 |

* $\frac{\text{(Product density)} \times (\Delta \text{ syringe volume}) \times 10^6}{\text{mass of blowdown}}$

**Typically, product is initially added (200 ppm) at twice the specified maintenance product feed rate (100 ppm). The concentration of treatment in the system will coincide with treatment feed rate (based on blowdown/syringe measurements) after about 150 hours.

The $VO_3^-$ ions were quantified by comparison of transmitted light with samples of known concentration as described above in the alternative sample analysis. Additionally, product feed rate was calculated from syringe pump and blowdown measurements. The active phosphate content was determined by persulfate oxidation of organophosphorus species to orthophosphate and subsequent formation of blue phosphomolybdate complex which was quantified photometrically; [refer to M. C. Rand; "Standard Methods for the Examination of Water and Wastewater", 14th Ed. (1975)].

Comparison of the treatment feed rate in the system predicted by the $VO_3^-$ ions versus the measurement of active phosphate demonstrates the superior accuracy of the measurement of $VO_3^-$ ions over the phosphate method. At an elapsed time of 324.67 hours, the active phosphate method indicated 30 ppm less than the accurate syringe pump and blowdown calculation. The difference in the levels arise from deposition of the organophosphorus components of the treatment onto the heat-exchanger tubes. At the same time, quantitative measurement of the $VO_3^-$ ions indicated only 7 ppm less than the calculated product level based on blowdown-/syringe feed measurements. The differences between the $VO_3^{31}$ ion level(s) and the total phosphorus level is a good indication of treatment effectiveness, since it quantifies how much of the active phosphorus-containing components are being lost within the system from deposition and corrosion processes. In an "ideal" operating system, the total phosphorus and $VO_3^-$ ion levels would all indicate an identical treatment concentration.

Comparison of Vanadate Ion Tracers ($VO_3^-$) with Chromate Ion Tracers ($Cr_2O_7^{-2}$)

A single water treatment formulation containing 53.15 weight percent deionized water, 16.1 weight percent sodium hydroxide (50 Weight percent aqueous), 7.0 weight percent amino-tris (methylene phosphoric acid) (Dequest 2000 manufactured by Monsanto), 12.0 weight percent organo phosphonocarboxylic acid (50 weight percent aqueous), 4.7 weight percent sodium tolyltriazole (50 weight percent aqueous), 2.5 weight percent fatty dicarboxylic acid (Diacid 1550 distributed by WestVaco), 2.0 weight percent surfactant, 1.4 weight percent sodium dichromate dihydrate and 1.15 weight percent ammonium metavanadate with the $VO_3^-$ tracer level controlled at 0.5 ppm V at a 100 ppm product level. PCT test results are summarized in Table 6.

TABLE 6

Chemical Feed Concentration Determination Based on $VO_3^-$ Concentration and $Cr_2O_7^{-2}$ Concentration

| Time Elasped (Hr) | pH | Calculated Concentration of Chemical Feed (ppm)* | |
|---|---|---|---|
| | | Based on $VO_3^-$ | Based on $Cr_2O_7^{-2}$ |
| 0 | 7.4 | 196 | 192 |
| 8.48 | — | 193 | 175 |
| 23.77 | 8.44 | 171 | 155 |
| 33.15 | 8.47 | 160 | 147 |
| 41.42 | — | 160 | 150 |
| 49.72 | 8.73 | 152 | 146 |
| 58.92 | 8.73 | 143 | 136 |
| 80.00 | 8.50 | 130 | 126 |
| 110.50 | 8.51 | 116 | 112 |
| 141.83 | 8.67 | 111 | 105 |
| 172.83 | 9.20 | 110 | 102 |
| 202.67 | 8.43 | 108 | 103 |
| 210.92 | 9.00 | 108 | 107 |
| 212.17 | 4.90** | 131 | 24 |
| 213.17 | 4.90** | 119 | 2 |
| 214.17 | 4.90** | 115 | 2 |
| 215.17 | 5.40** | 112 | 2 |
| 216.17 | 7.7** | — | 10 |
| 216.87 | 7.86** | — | 11 |
| 217.17 | 7.9** | 112 | 11 |
| 218.17 | 8.1** | 99 | 11 |
| 222.27 | 8.37 | 76 | 11 |
| 234.75 | 8.3 | 56 | 16 |
| 270.60 | 8.45 | 46 | 16 |
| 321.83 | 8.50 | 72 | 50 |
| 383.72 | — | 77 | 60 |

*Typically, product is initially added (200 ppm) at twice the specified maintenance product feed rate (100 ppm). The concentration of treatment in the system will coincide with treatment feed rate (based on blowdown/syringe measurements) after about 150 hours.
**Out-of-specification operation to test effects of low pH excursion.

The unknown quantities of $VO_3^-$ ions were quantified by comparison of transmitted light with samples of known concentration. Transmittance was determined with a Bausch and Lomb Spectrometer 2000.

Comparison of the treatment feed rate in the system predicted by the $VO_3^-$ ions versus the measurement of $Cr_2O_7^{-2}$ tracer demonstrates the superior accuracy of the measurement $VO_3^-$ ions over that of $Cr_2O_7^{-2}$ ions when pH excursions occur. The data as shown in Table 5 reflects an acid upset initiated at an elapsed time of 210.92 hours. The low pH causes a sharp rise in mild steel corrosion rate of the heat exchanger which is known to cause losses of the bichromate tracer. The vanadate is noticeably more resistant to that loss than bichromate as shown in FIG. 4. Also shown in FIG. 4, the vanadate tracer recovers more quickly than the bichromate.

EXAMPLE 3 — Conclusion

The benefits of using vanadium compounds are as follows:

Vanadium oxyanions ($VO_3^-$) does not tend to precipitate with other solids which are formed between pH 7-9.

Vanadium oxyanions ($VO_3^-$) are resistant to precipitation in the presence of corroding mild steel heat exchange tubes.

EXAMPLE 4

Several transition metal ions were evaluated in aqueous systems at pH 9.3 and pH 7.0. The performance of each ion and oxyion was determined by the following equation:

% Recovery=$(FS / US) \times 100\%$;

wherein:

FS=Concentration of metal ion (ppm) in filtered sample after passing through 0.45 $\mu$m filter
US=Initial concentration of transition metal ion (ppm) in unfiltered sample A maximum value of %Recovery=100% shows that the transition ion was completely soluble in the system at the given pH. Results are shown in Table 7 and Table 8 below.

TABLE 7

Performance Comparisons of Transition Metal Tracers (at pH 7)

| Metal Ion | Element Form Used | Transition Element Group Number Periodic Table | % Recovery |
|---|---|---|---|
| Silver | $Ag^+$ | IB | 22% |
| Zinc | $Zn^{+2}$ | IIB | 97% |
| Yttrium | $Y^{+3}$ | IIIB | 91% |
| Zirconium | $Zr^{+4}$ | IVB | 8% |
| Vanadium | $V^{+5}$* | VB | 100% |
| Chromium | $Cr^{+3}$** | VIB | 99% |
| Manganese | $Mn^{+2}$ | VIIB | 98% |
| Nickel | $Ni^{+2}$ | VIIIB (col. 3) | 100% |
| Cobalt | $Co^{+2}$ | VIIIB (col. 2) | 95% |
| Aluminum | $Al^{+3}$ | IIIB | 70% |

*as Vanadate ($VO_3^-$).
**Note distinction from chromate ($Cr_2O_7^{-2}$), where $Cr^{+6}$ is formal oxidation state of metal center.

TABLE 8

Performance Comparisons of Transition Metal as Tracers (at pH 9.3)

| Metal Ion | Element Form Used | Transition Element Group Number Periodic Table | % Recovery |
|---|---|---|---|
| Silver | $Ag^+$ | IB | 28% |
| Zinc | $Zn^{+2}$ | IIB | 36% |
| Yttrium | $Y^{+3}$ | IIIB | 63% |
| Zirconium | $Zr^{+4}$ | IVB | 6% |
| Vanadium | $V^{+5}$* | VB | 100% |
| Chromium | $Cr^{+3}$** | VIB | 94% |
| Manganese | $Mn^{+2}$ | VIIB | 73% |
| Nickel | $Ni^{+2}$ | VIIIB (col. 3) | 67% |
| Cobalt | $Co^{+2}$ | VIIIB (col. 2) | 50% |
| Aluminum | $Al^{+3}$ | IIIB | 60% |

*as Vanadate ($VO_3^-$).
Note distinction from chromate ($Cr_2O_7^{-2}$), where $Cr^{+6}$ is formal oxidation state of metal center.

As shown in Table 7 and Table 8, Vanadium ($VO_3^-$) and Chromium ($Cr^{+3}$) exhibit excellent solubility in both systems, whereas other transition metals such as zinc ($Zn^{+2}$), yttrium ($Y^{+3}$), nickel ($Ni^{+2}$) and cobalt ($Co^{+2}$) are better suited in systems with a pH 7.0 than pH 9.3. Solubility at lower pH for these transition metals show an advantage over non-transition metals such as aluminum ($Al^{+3}$) which are not as soluble at pH 7 as shown in Table 7. Furthermore, Table 7 and Table 8 show that silver ($Ag^{30}$) and zirconium ($Zr^{+4}$) are not suitable at either pH 7 or pH 9.3.

CONCLUSION

While the invention has been described in connection with specific embodiments thereof, it will be understood that it is capable of further modifications. This application is intended to cover any variations, uses or adaptions of the invention following, in general, the principles of this invention, and including such departures from the present disclosure as come within known and customary practice within the art to which the invention pertains.

What is claimed is:

1. A method for monitoring the composition of a liquid system which comprises adding a quantity of a transition metal compound to said liquid system and detecting the amount of said transition metal compound within one or more samples of said liquid system, wherein the quantity of transition metal compound detected within the samples corresponds to the concentration of one or more treating agents of said liquid system, wherein the transition metal compound is in the form of ions, cations, oxyanions or other charged radicals which are soluble in said liquid system, and wherein said transition metal compound contains a transition metals selected from the group consisting of yttrium, zinc, vanadium, manganese, nickel, cobalt, molybdenum, and chromium (III).

2. A method as in claim 1 wherein the liquid system is subject to changes in temperature and pressure and to the addition of chemical treatment agents.

3. A method as in claim 1 wherein
   (A) the liquid system is aqueous and contains an amount of treating agent which is susceptible to deposition on equipment scale or degradation;
   (B) the quantity of transition metal compound added is proportional to the amount of treating agent added to the liquid system; and
   (C) the transition metal compound is inert in said liquid system and exhibits a lower DER value than the treating agent.

4. A method as in claim 3 wherein one or more parameters that are monitored are selected from:
   (1) the present volume of the aqueous liquid system;
   (2) the changes in volume of the aqueous liquid system;
   (3) the quantity of treating agent added to the aqueous liquid system;
   (4) the changes in the concentration of the treating agent within the aqueous liquid system; and
   (5) the lifetime of the treating agent within the aqueous liquid system.

5. A method as in claim 3 comprising the additional step of adjusting the concentration of one or more treating agents in the aqueous liquid system based on the quantity of transition metal compound determined within the samples of said aqueous liquid system.

6. A method as in claim 5 wherein the additional step of adjusting the concentration of one or more treating agents in the aqueous liquid system comprises adding an amount of water or treating agent to the aqueous liquid system.

7. A method as in claim 3 wherein the aqueous liquid system is selected from static systems, open-ended systems, closed-end systems and once-through systems.

8. A method as in claim 7 wherein the aqueous liquid system is a cooling water system which experiences evaporative losses of water and the treatment agent is selected from scale inhibitors and corrosion inhibitors.

9. A method as in claim 3 wherein the amount of said transition metal compound is detected in samples taken from different locations within the aqueous liquid system.

10. A method as in claim 3 wherein a portion of the aqueous liquid is continuously removed from the aqueous liquid system and the aqueous liquid system is supplemented with makeup water.

11. A method as in claim 10 wherein the background concentration of the transition metal within the makeup water for the aqueous liquid system is less than 0.5 ppm.

12. A method as in claim 10 wherein the background concentration of the transition metal within the makeup water for the aqueous liquid system is less than 0.01 ppm.

13. A method in accordance with claim 3 wherein the aqueous liquid system contains two or more treating agents together with two or more different transition metals.

14. A method a s in claim 3 wherein the transition metal is quantified within the samples of aqueous liquid system by visual calorimetric methods, spectrophotometric methods, the transmission of light or the absorption of ultraviolet and visible light.

15. A method as in claim 3 wherein the sample of the aqueous liquid system is treated with a masking agent prior to quantifying the amount of transitional metal therein.

16. A method as in claim 3 wherein the transition metal within the aqueous liquid system is reacted with a color reagent to enhance detection.

17. A method as in claim 1 where in the treatment agent is selected from the group consisting of polymeric scale inhibitors, phosphates and organo-phosphates.

18. A method as in claim 1 wherein the deposit enrichment ratio of the transition metal is below 1.

19. A method as in claim 1 wherein the deposit enrichment ratio of the transition metal is below 1.

20. A method for monitoring the composition of a cooling water system which contains a treating agent wherein said method comprises adding a known quantity of a cobalt compound to said cooling water system which is proportional to the treating agent added and detecting the amount of cobalt ions, cations, oxyanions or other charged radicals within samples of said cooling water system wherein the quantity of cobalt detected within the samples corresponds to the concentration of one or more components of said cooling water system.

21. A method for monitoring the composition of a cooling water system which contains a treating agent wherein said method comprises adding a known quantity of a vanadium compound to said cooling water system which is proportional to the treating agent added and detecting the amount of vanadium ions, cations, oxyanions or other charged radicals within samples of said cooling water system wherein the quantity of vanadium detected within the samples corresponds to the concentration of one or more components of said cooling water system.

22. A method for monitoring the composition of a cooling water system as in claim 21 comprising the additional step of oxidizing said vanadium within at least one but not all of said samples with an oxidizing agent, wherein said detected amount of vanadium is obtained by a calorimetric comparison of said samples with oxidized vanadium with said samples without oxidized vanadium.

23. A method for monitoring the composition of a cooling water system as in claim 22 wherein said oxidizing agent is added and completely reacted with said vanadium ions, cations, oxyanions and other charged radicals before a color reagent is added.

24. A method for monitoring one or more parameters of a cooling water system as in claim 23 wherein said color reagent is a PAR solution.

25. A method for monitoring one or more parameters of a cooling water system as in claim 23 wherein said oxidizing agent is $H_2O_2$.

26. A method for monitoring the composition of a cooling water system as in claim 23 wherein said vanadium ions, cations, oxyanions and other charged radicals are oxidized to form 2:1 peroxyvanadate.

27. A method for monitoring the composition of a cooling water system which contains a treating agent wherein said method comprises the following steps:
 (i) adding a known quantity of a vanadium compound to said cooling water system which is proportional to the treating agent added; and
 (ii) detecting the amount of vanadium ions, cations, oxyanions and other charged radicals within samples taken from said cooling water system;
wherein said detecting step includes treating at least one but not all of said samples of cooling water with $H_2O_2$ prior to adding a color reagent and wherein the quantity of vanadium compound detected corresponds to the concentration of one or more compounds of the liquid system.

28. A method for monitoring one or more parameters of a cooling water system which contains a treating agent as in claim 27 wherein said detecting step includes obtaining the difference in transmittance of said samples with treated vanadium with the transmittance of said samples without treated vanadium.

* * * * *